United States Patent [19]

Toth

[11] 4,011,248
[45] Mar. 8, 1977

[54] ORGANIC COMPOUNDS

[75] Inventor: Istvan Toth, Bottmingen, Switzerland

[73] Assignee: Sandoz Ltd., Basel, Switzerland

[22] Filed: Dec. 1, 1975

[21] Appl. No.: 636,816

[30] Foreign Application Priority Data

Dec. 5, 1974 Switzerland ............... 16158/74

[52] U.S. Cl. .............................................. 260/369
[51] Int. Cl.$^2$ ........................................ C09B 1/00
[58] Field of Search ................................. 260/369

[56] References Cited

UNITED STATES PATENTS

| | | | |
|---|---|---|---|
| 3,786,073 | 1/1974 | Frey et al. | 260/369 |
| 3,798,244 | 3/1974 | Mueller et al. | 260/369 |
| 3,868,395 | 2/1975 | Bantel et al. | 260/369 |
| 3,904,659 | 9/1975 | Bantel et al. | 260/369 |
| 3,931,251 | 1/1976 | Vogel et al. | 260/369 |

*Primary Examiner*—Paul F. Shaver
*Attorney, Agent, or Firm*—Gerald D. Sharkin; Richard E. Vila; Thomas C. Doyle

[57] ABSTRACT

The present invention concerns a novel process for the purification of 1-nitroanthraquinone containing dinitroanthraquinone as impurity which comprises selectively converting the dinitroanthraquinone to an amino derivative by treatment of the mixture with ammonia, converting the resulting amino derivative to acid addition salt form, and separating the acid addition salt form of the amino derivative from the 1-nitroanthraquinone on the basis of their different polarities.

11 Claims, No Drawings

ORGANIC COMPOUNDS

The present invention relates to a process for the purification of 1-nitroanthraquinone, and more specifically for the purification of 1-nitroanthraquinone containing dinitroanthraquinone as impurity.

Accordingly, the present invention provides a process of purifying 1-nitroanthraquinone in admixture with dinitroanthraquinone as impurity which comprises selectively converting the dinitroanthraquinone to an amino derivative by treatment of the mixture with ammonia, converting the resulting amino derivative to acid addition salt form, and separating the acid addition salt form of the amino derivative from the 1-nitroanthraquinone on the basis of their different polarities.

The present invention is thus based on the discovery that the rate of ammoniation of the dinitroanthraquinones is substantially higher than that of 1-nitroanthraquinone.

Separation of the acid addition salt of the amino derivative, which is normally the corresponding diaminoanthraquinone, from the 1-nitroanthraquinone on the basis of their different polarities is conveniently effected on the basis of their substantially different solubilities in polar and non-polar solvents.

The process is particularly suited to the purification of 1-nitroanthraquinone produced by the nitric acid nitration of anthraquinone in the absence or presence of aids such as sulphuric or phosphoric acid. Typical impurities are thus mainly 1,5- and 1,8-dinitroanthraquinone, with possible amounts of 1,6-, 1,7-, 2,6- and/or 2,7-dinitroanthraquinone as well as 2-nitroanthraquinone.

The amount of impurity is in principle not critical, although for practical reasons the 1-nitroanthraquinone preferably contains at most 50%, particularly 40%, especially at most 30% or even 20% by weight impurity.

The ammonia employed for the selective conversion of the dinitroaminoanthraquinone to the amino-derivative may in part or completely be generated in situ, e.g. from ammonium carbonate or urea with heating, although preferably ammonia gas or an aqueous solution thereof, e.g. a 25% by weight aqueous solution, is employed.

The reaction is suitably effected in a solvent or suspension medium, the type of which is not critical. Preferably, however, there is employed as solvent or suspension medium an ether, especially an aralkyl ether such as the ethers of, on the one hand, mono- or polydric phenols unsubstituted or mono- or di-substituted by alkyl ($C_1$–$C_5$) with $C_1$–$C_5$ in the aggregate of the alkyl substituents, and, on the other hand, an aliphatic alcohol ($C_1$–$C_5$), especially the ethers anisole, phenetole, hydroquinone-dimethyl ether and resorcinoldimethyl ether. Preferably a solvent as opposed to a suspension medium is employed, particularly a non-polar, water immiscible solvent and/or when employed to give a concentrated solution, i.e. between saturation and one-tenth saturation, preferably between saturation and one-fifth saturation.

The amount of ammonia employed naturally depends on the amount of dinitroanthraquinone impurity. Preferably at least a stoichiometric amount is employed, i.e. at least 1 mol, preferably at least 2 mols, of ammonia per mol of dinitroanthraquinone.

The conversion of the dinitroanthraquinone to the amino derivative may be effected at atmospheric or at higher pressure, e.g. from 1 to 15 bar, preferably from 1 to 5 bar. Preferably the conversion is effected at an elevated temperature, e.g. 50° to 300°, more preferably 100° to 200° C. When the ammonia is produced in situ, naturally the temperature employed must be appropriate to the mode of ammonia generation, e.g. at least 58° or 133° C in the production of ammonia from ammonium carbonate or urea, respectively.

The course of ammoniation may be monitored employing conventional techniques, for example T.L.C. or gas chromatography techniques, to determine when all the dinitroanthraquinone has reacted, at which stage the reaction is terminated.

After the reaction, the amino derivative is converted to acid addition salt form, e.g. the hydrochloride, hydrogen sulphate or hydrogen phosphate form, in conventional manner, e.g. by addition of a dilute mineral acid, e.g. hydrochloric, sulphuric or phosphoric acid, to the reaction mixture with stirring and if necessary heating, e.g. from 100° C to boiling-point temperature. The acid addition salt form may be separated off in conventional manner, e.g. by partitioning off the aqueous phase, if necessary first taking up the 1-nitroanthraquinone in a non-polar, water immiscible solvent such as anisole or phenetole. The 1-nitroanthraquinone of the organic phase may be obtained by distilling off the solvent, or may be employed in solution for subsequent treatment.

Any 2-nitroanthraquinone present may be removed in conventional manner, e.g. by the known sulphite purification or by selective recrystallisation either before or after the process of the present invention is employed.

The 1-nitroanthraquinone is a valuable and well-known intermediate employed in known manner in the production of known anthraquinone dyestuffs.

The invention is illustrated by the following Example.

Ammonia gas at a pressure of 2–3 bar is continuously admitted into an autoclave containing 100 gm of impure 1-nitroanthraquinone (for exact composition, see below) in 500 gm anisole at a temperature of 175° C. The course of the reaction is periodically monitored by gas chromatography. When it is found that all dinitroanthraquinone originally present has been converted to the amino derivative (about 5 to 6 hours) the reaction is terminated and the reaction mixture extracted at 120° to 130° C with 100 ml portions of 75% by weight $H_2SO_4$ until the remaining anisole solution is practically colourless (between 3 to 5 extractions). The acid addition salt $H_2SO_4$ portions are combined and diluted with water to 10% by weight strength $H_2SO_4$, the acid addition salts then being separated off by precipitation and filtration. The anisole of the anisole phase is distilled off leaving almost pure 1-nitroanthraquinone (for composition, see below).

Yield
72 gm 1-nitroanthraquinone
24 gm amino derivative

| Composition of the initial and final products | | |
| --- | --- | --- |
|  | Initial Product* | Final Product* |
| Anthraquinone | 1.5% | 2% |
| 1-Nitroanthraquinone | 80% | 97% |
| 1,5-Dinitroanthraquinone | 10.5% | 0.1% |

| Composition of the initial and final products | | |
|---|---|---|
| | Initial Product* | Final Product* |
| 1,8-Dinitroanthraquinone | 8% | 0.1% |

The Example is repeated admitting the ammonia gas discontinuously with similar results.

The Example is repeated employing crude 1-nitroanthraquinone of the following composition, 66% 1-Nitroanthraquinone
3.5% Anthraquinone
7% 1,5-Dinitroanthraquinone
7% 1,8-Dinitroanthraquinone
7% 1,6-Dinitroanthraquinone
7% 1,7-Dinitroanthraquinone
2.5% 2-Nitroanthraquinone, 60 gm of said 1-nitroanthraquinone being dissolved in 450 parts of anisole and ammoniation taking place at 170° C at 2 atmospheres pressure. Ammoniation was terminated in a first run after 3 hours and in a second run after 5 hours. Subsequent treatment involved washing four times at 100° C with four 50 ml portions of 65% by weight $H_2SO_4$ and then with a mixture of 25 ml water, 25 ml of 25% by weight $NH_4OH$ and 7 gm $(NH_4)_2SO_4$. After distilling off the anisole, washing twice with 20 ml portions of anisole and then with 300 ml of hot water, the resulting product was dried at 130° C.

Composition of product of first run:
97% 1-Nitroanthraquinone
0.6% Anthraquinone
<0.5% 1,5-Dinitroanthraquinone
0.0% 1,8-Dinitroanthraquinone
<0.5% 1,6-Dinitroanthraquinone
<0.5% 1,7-Dinitroanthraquinone
<0.5% 2-Nitroanthraquinone
Yield: 27.1 gm Composition of product of second run:
97.5% 1-Nitroanthraquinone
1% Anthraquinone
<0.7% 2-Nitroanthraquinone
<0.3% 1,5-Dinitroanthraquinone
<0.3% 1,6-Dinitroanthraquinone
<0.3% 1,7-Dinitroanthraquinone
Yield: 29.1 gm

What is claimed is:

1. A process of purifying 1-nitroanthraquinone in admixture with dinitroanthraquinone as impurity which comprises selectively converting the dinitroanthraquinone to an amino derivative by treatment of the mixture with ammonia, converting the resulting amino derivative to acid addition salt form, and separating the acid addition salt form of the amino derivative from the 1-nitroanthraquinone on the basis of their different polarities.

2. A process according to claim 1, wherein the ammonia treatment is carried out in a non-polar, water immiscible solvent.

3. A process according to claim 2, wherein the acid addition salt is formed by the addition of aqueous acid to the reaction mixture and separation is effected by partitioning off either the organic or aqueous phase.

4. A process according to claim 2, wherein said non-polar solvent is an aryl-alkyl ether.

5. A process according to claim 4, wherein said ether is anisole or phenetole.

6. A process according to claim 1, wherein hydrochloric, sulphuric or phosphoric acid is employed for acid addition salt formation.

7. A process according to claim 6, wherein sulphuric acid is employed.

8. A process according to claim 1, wherein ammonia treatment is effected directly employing gaseous or aqueous ammonia.

9. A process according to claim 1, wherein the ammonia treatment is effected at a temperature of from 50° to 300° C.

10. A process according to claim 1, wherein the ammonia treatment is effected at a pressure of from 1 to 15 bar.

11. A process according to claim 8 wherein the 1-nitroanthraquinone contains, at most, 50% di-nitroanthraquinone and the ammonia treatment is effected at a temperature of 100°–200° C. employing at least 2 mols of ammonia per mol of di-nitroanthraquinone.

* * * * *